(12) United States Patent
Lemmer et al.

(10) Patent No.: US 7,739,919 B2
(45) Date of Patent: Jun. 22, 2010

(54) TEST SPECIMEN HOLDER

(75) Inventors: Steven Ray Lemmer, Norwood, MN (US); Steven E. Sikkila, Minnetonka, MN (US)

(73) Assignee: MTS Systems Corporation, Eden Prairie, MN (US)

( * ) Notice: Subject to any disclaimer, the term of this patent is extended or adjusted under 35 U.S.C. 154(b) by 0 days.

(21) Appl. No.: 11/558,595

(22) Filed: Nov. 10, 2006

(65) Prior Publication Data

US 2007/0107534 A1  May 17, 2007

Related U.S. Application Data

(60) Provisional application No. 60/735,533, filed on Nov. 10, 2005.

(51) Int. Cl.
*G01N 3/02* (2006.01)
(52) U.S. Cl. .................................................. 73/857
(58) Field of Classification Search ............. 73/857
See application file for complete search history.

(56) References Cited

U.S. PATENT DOCUMENTS

| | | | |
|---|---|---|---|
| 2,133,874 A * | 10/1938 | Sparks | 72/128 |
| 3,224,289 A | 12/1965 | Palm | |
| 3,388,592 A | 6/1968 | Griffiths | |
| 3,908,449 A * | 9/1975 | Zuber | 73/857 |
| 4,019,378 A | 4/1977 | Keller et al. | |
| 4,537,080 A | 8/1985 | Christiansen | |
| 4,721,000 A * | 1/1988 | Scanlon | 73/833 |
| 5,095,757 A * | 3/1992 | Larsen et al. | 73/857 |
| 5,195,378 A * | 3/1993 | Ferguson | 73/790 |
| 5,365,765 A * | 11/1994 | Gohl et al. | 72/355.6 |
| 5,421,205 A * | 6/1995 | Pohl | 73/833 |
| 6,629,466 B2 | 10/2003 | Grote et al. | |
| 6,805,827 B2 * | 10/2004 | Kami et al. | 264/328.1 |

FOREIGN PATENT DOCUMENTS

| | | |
|---|---|---|
| GB | 1196540 A | 6/1970 |
| SU | 729481 A1 | 4/1980 |

OTHER PUBLICATIONS

Drawings illustrating a test specimen holder sold or offered for sale in the U.S. before Nov. 9, 2005.
Official Search Report and Written Opinion of the European Patent Office in counterpart foreign application No. PCT/US2006/044022 filed Nov. 10, 2006.
Drawings illustrating a pipe/tube test specimen holder sold or offered for sale in the U. S. before Nov. 10, 2004.

* cited by examiner

*Primary Examiner*—Lisa M Caputo
*Assistant Examiner*—Octavia Davis
(74) *Attorney, Agent, or Firm*—Steven M. Koehler; Westman, Champlin & Kelly, P.A.

(57) ABSTRACT

A test specimen holder includes at least one pair of wedges, a plurality of pistons and a tie bar connected to each of the pistons. A single cylinder body is operable with each of the pistons and the wedges. The cylinder body is adapted to urge the wedges together with relative movement of the cylinder body with respect to the pistons.

7 Claims, 8 Drawing Sheets

TEST SPECIMEN HOLDER

CROSS-REFERENCE TO RELATED APPLICATION

The present application is based on and claims the benefit of U.S. provisional patent application Ser. No. 60/735,533, filed Nov. 10, 2005, the content of which is hereby incorporated by reference in its entirety.

BACKGROUND

The discussion below is merely provided for general background information and is not intended to be used as an aid in determining the scope of the claimed subject matter.

Test specimen holders or grips are well known in the material testing art and are used frequently to hold a test specimen in a material testing system. The holder includes opposed jaws or wedges operated by a piston that grips the test specimen therebetween. Fluid pressure (hydraulic or pneumatic) pressurizes the piston chamber to operate the jaws. Preferably, the jaws grip the test specimen without altering the vertical position of the jaws on the test specimen, thereby making it possible to preselect the exact point at which the specimen will be held in order not to impart tension loads during placement of the test specimen in the material testing system. Difficulties arise when large test specimens are to be tested, particularly when a planar test specimen must be gripped along a long lateral edge.

SUMMARY

This Summary and the Abstract are provided to introduce some concepts in a simplified form that are further described below in the Detailed Description. The Summary and Abstract are not intended to identify key features or essential features of the claimed subject matter, nor is it intended to be used as an aid in determining the scope of the claimed subject matter. In addition, the description herein provided and the claimed subject matter should not be interpreted as being directed to addressing any of the short-comings discussed in the Background.

A test specimen holder includes at least one pair of wedges, a plurality of pistons and a tie bar connected to each of the pistons. A single cylinder body is operable with each of the pistons and the wedges. The cylinder body is adapted to urge the wedges together with relative movement of the cylinder body with respect to the pistons.

DETAILED DESCRIPTION

Figure 1:
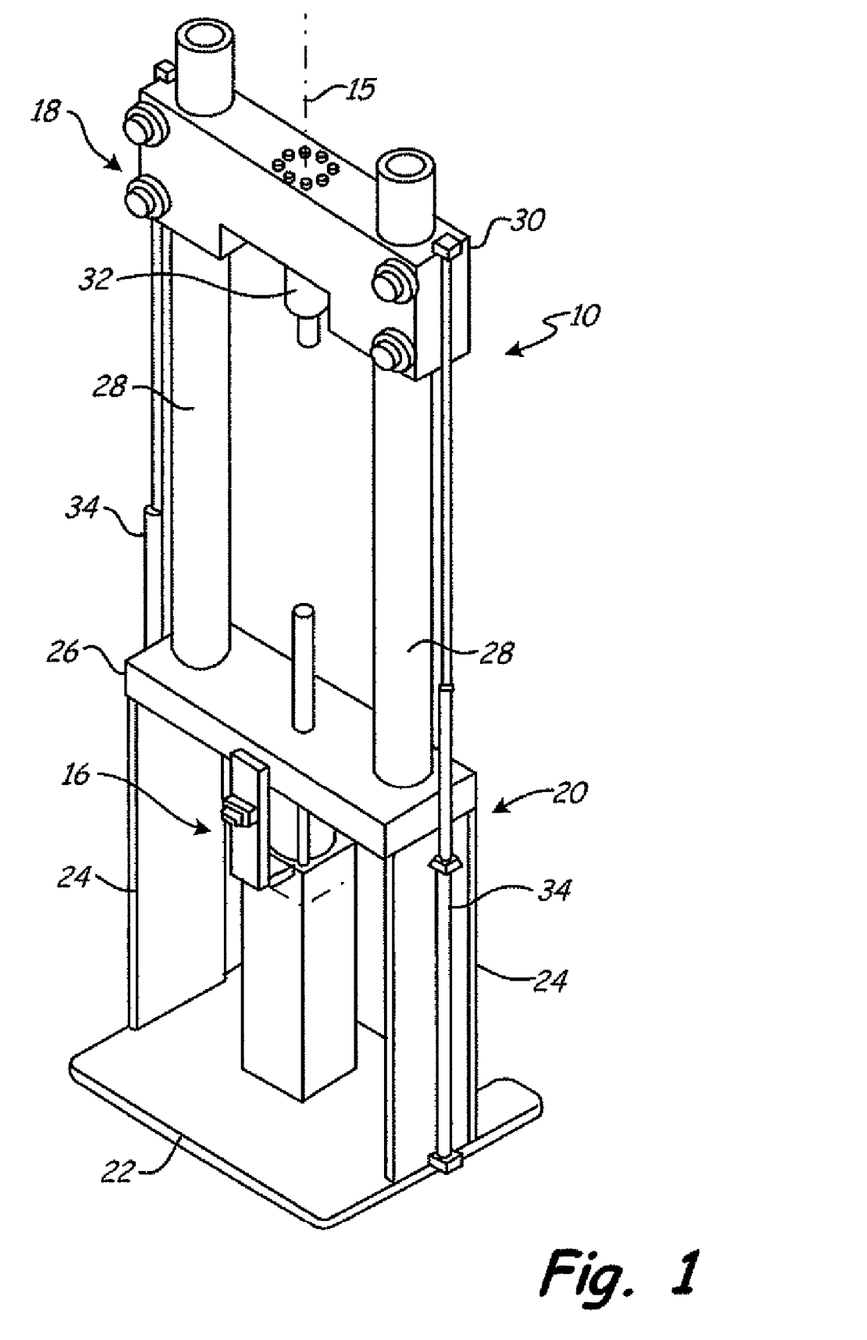
FIG. 1 is a perspective view of a load frame.
Figure 2:
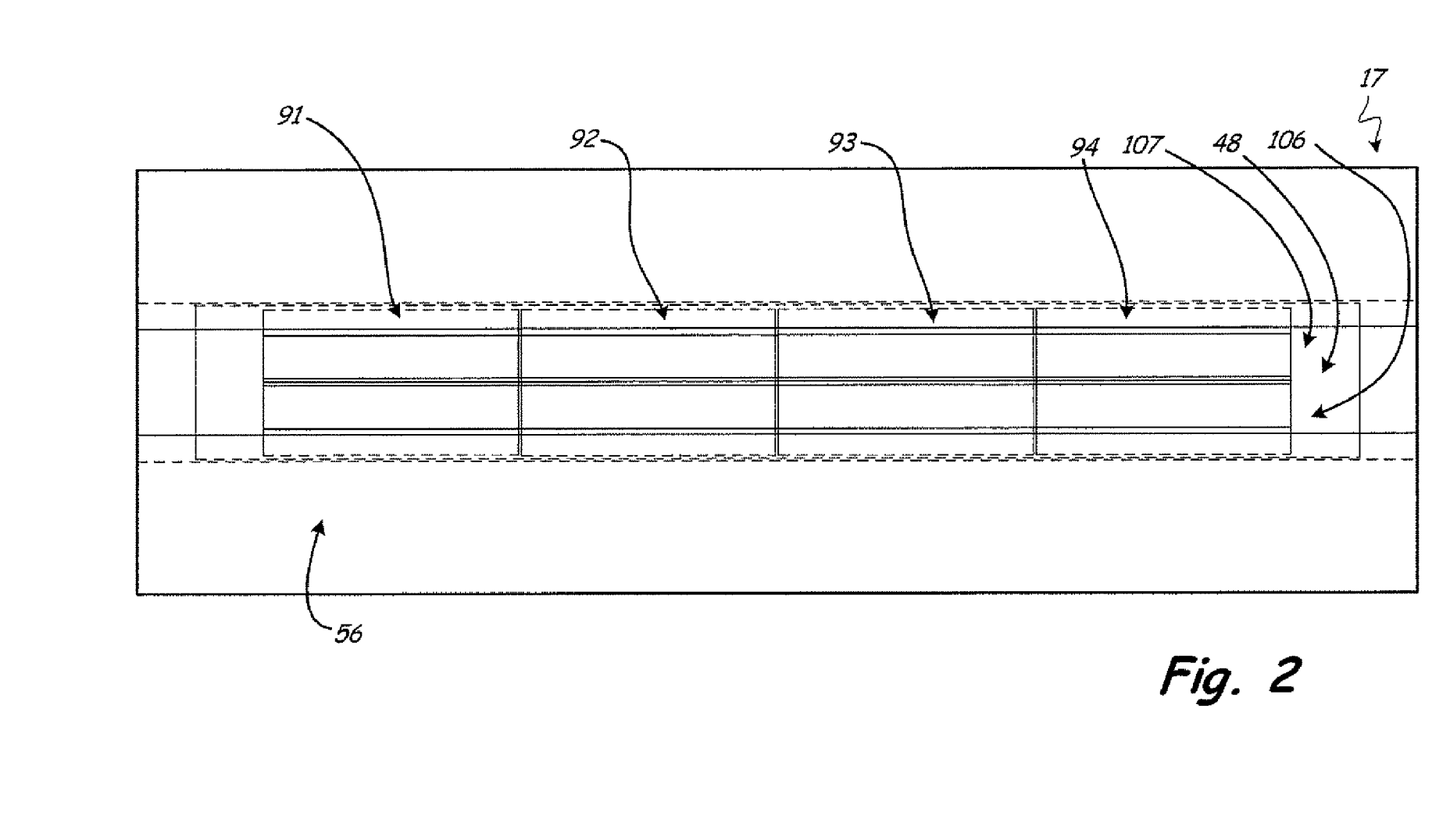
FIG. 2 is a top view of a test specimen holder.

A material testing system 10 for applying force loads to a planer test specimen is illustrated in FIG. 1. The system 10 typically would include an upper test specimen holder and an identical lower test specimen holder both of the type illustrated and described below. The test specimen holders hold a test specimen along a longitudinal axis 15. In the embodiment illustrated, the lower test specimen holder is connected to an actuator 16 through which force loads are applied to the test specimen and reacted against a reaction structure generally indicated at 18.

In the exemplary embodiment illustrated, the material testing system 10 includes a frame 20 having a base 22. A pair of support members 24 extend upwardly from the base 22 and are joined together by a crossbeam 26 which provides a stable support surface. A pair of support columns 28 extend upwardly from the crossbeam 26 to a movable crosshead 30. A load cell 32 joins the upper test specimen holder to the crosshead 30. As is known in the art, the load cell 32 provides a signal indicative of tension or compression forces applied to the test specimen. The crosshead 30 and the support columns 28 provide the reaction structure 18. Hydraulic lifts 34 move the crosshead 30 to selectively fixed positions.

Referring to FIGS. 2-5, a test specimen holder 17 is particularly useful for holding a planer test specimen such as but not limited to wide panels of sheet metal. The test specimen holder 17 applies uniform compression forces to an end portion of the planer test specimen, and also allows for faster loading and unloading of the test specimen.

One aspect of the test specimen holder is that it includes multiple grip assemblies formed from multiple pairs of movable wedges and multiple pistons. A single cylinder body operable with each of the pistons and the wedges is adapted to urge the movable wedges of each pair together.

Figure 3:
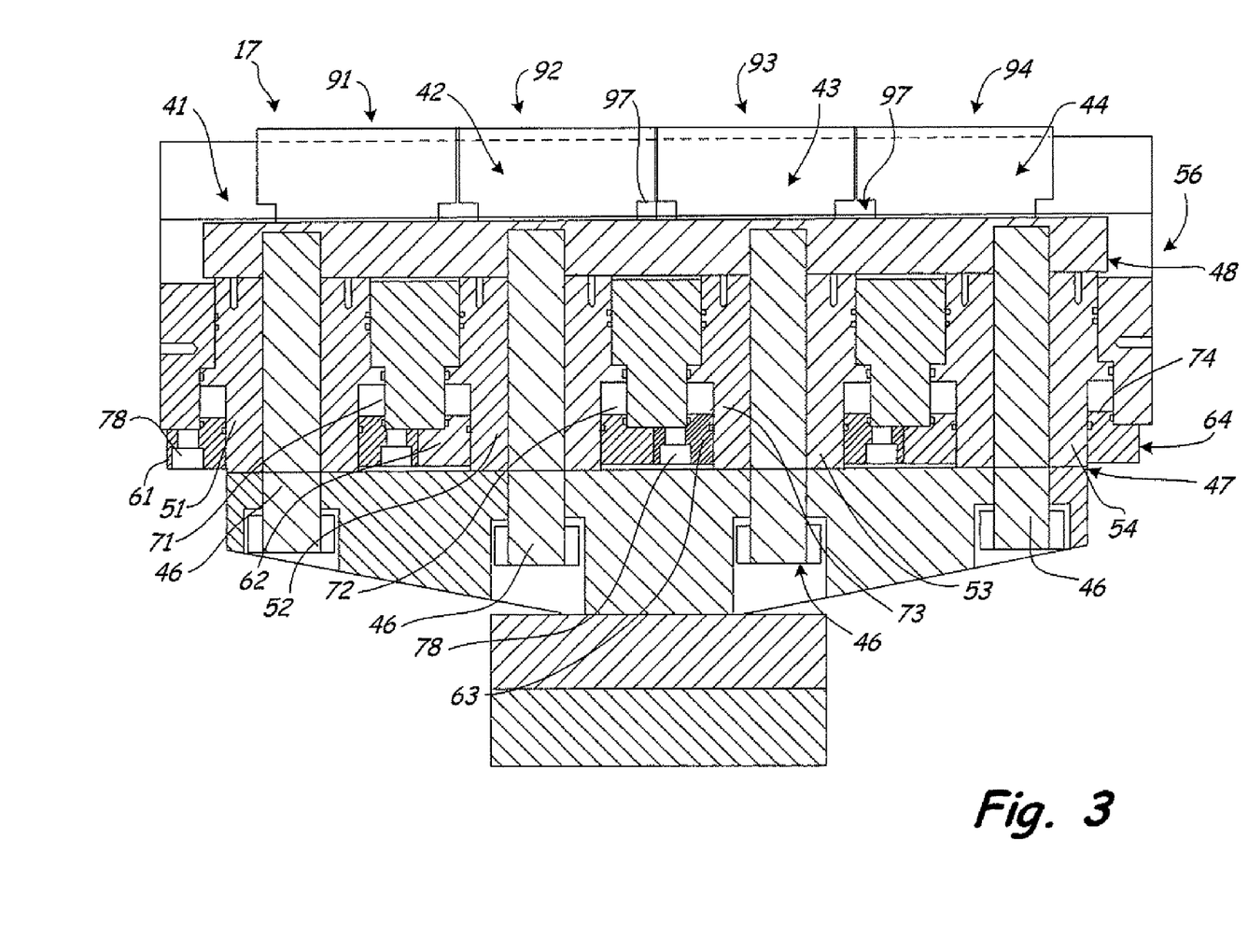
FIG. 3 is a side view of the test specimen holder.
Figure 4:
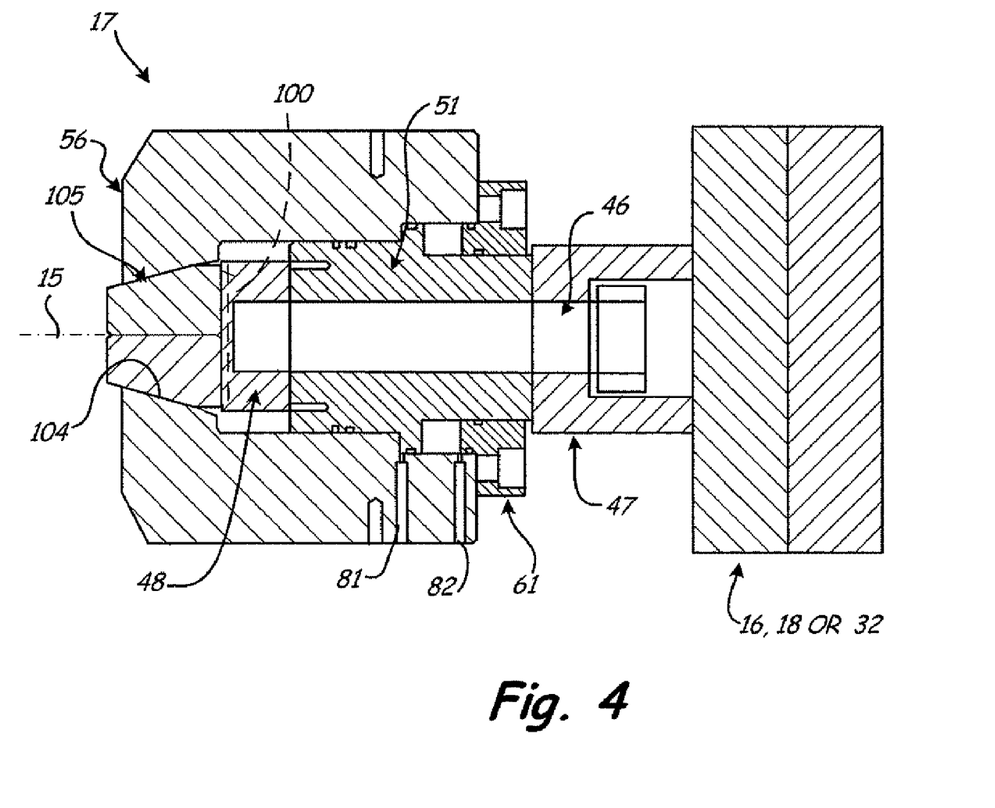
FIG. 4 is an end view of the test specimen holder.

Referring to FIGS. 3-4, test specimen holder 17 includes four gripping assemblies 41, 42, 43 and 44 by way of example. It should be understood that two or more gripping assemblies can be used in other forms of the test specimen holder 17. Each gripping assembly 41-44 is mounted to a mounting bar 47 with a suitable fastener 46 such as a mounting stud and preload nut herein illustrated. In particular, in the illustrated embodiment, each fastener 46 rigidly connects, under a selected preload force depending upon the application, a wedge plate 48 and a piston 51, 52, 53 and 54 to the mounting bar 47. In this manner, the pistons 51, 52, 53 and 54 act in unison since they are all rigidly connected to tie bar such as the mounting bar 47 and/or wedge plate 48. The single wedge plate 48 being connected to each of the fasteners 46 helps ensure a rigid connection; however, other techniques can be used so that the pistons act in unison and are rigidly connected to a form of tie bar such as the mounting bar 47 and/or wedge plate.

Each of the pistons 51-54 are disposed in a chamber formed in a cylinder body 56. In the embodiment illustrated, an integral cylinder body formed from a single unitary piece is used to form the single cylinder body 56. In other embodiments, multiple pieces can be used and fastened together to form the single cylinder body 56 having the chambers therein. End caps 61, 62, 63 and 64 are provided on an end of the cylinder body 56 to form a sealed chamber for each piston 51-54, with a sealed bore 71, 72, 73 and 74 allowing a portion of each piston 51-54 to extend therethrough for mounting to the mounting bar 47. Suitable fasteners such as threaded mounting bolts 78 are used to join the end caps 61-64 to the cylinder body 56. In the embodiment illustrated in FIG. 3, fasteners 78 are illustrated for use with end caps 61 and 63 where end caps 62 and 64 also have fasteners but are not shown since they are joined to other portions of the cylinder body 56.

The multiple grip assemblies 41-44 can either be pneumatically or hydraulically actuated with a suitable driving fluid being selectively provided to the chambers from a fluid source not shown. Ports such as illustrated in FIG. 5 at 81, 82 are provided to each chamber on opposite sides of each piston in order to cause movement of the cylinder body 56 relative to the pistons 51-54 as desired.

Figure 5:
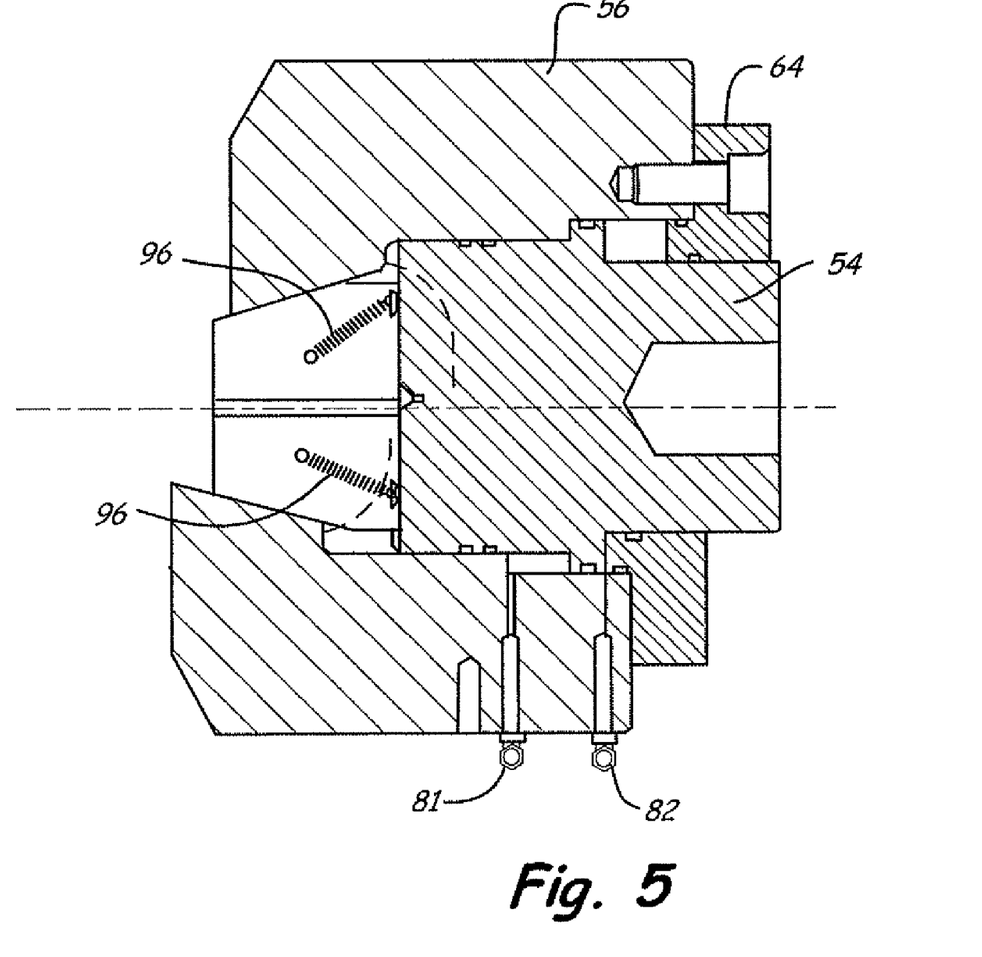
FIG. 5 is an end view of the test specimen holder illustrating operation thereof.

Each of the pairs of wedges 91, 92, 93 and 94 are disposed on the wedge plate 48 (or directly on the pistons as illustrated in FIG. 5) for sliding movement away from and towards each other. Springs 96 (FIG. 5) can be provided on each side of each of the wedges. In the embodiment of FIG. 5, the springs 96 join the wedge to the pistons; however, the springs can be joined to the wedge plate 48, if present. Each spring 96 applies a force to the wedge urging it away from the opposed wedge. Gaps 97 (FIG. 3) can be provided to accommodate the springs 96.

To limit undesirable sliding movement of the wedges laterally (towards and away from adjacent wedges on the same side of the test specimen), guide assemblies can be used. In other words, the guide assemblies allow guided movement of the wedges toward and away from each other and limit movement transverse to the guided movement. In the embodiment illustrated in FIG. 4, a groove 100 is provided in the wedge plate 48 where a portion of each wedge of each pair 91-94 extends into the corresponding groove 100 allowing sliding movement toward and away from each other as a pair, but inhibiting sliding movement transverse to the groove 100. If desired, grooves can be provided in the wedges and corresponding protrusions can be provided on the wedge plate 48.

Referring to FIG. 4, each of the wedges contact inclined surfaces 104,105 on the cylinder body 56. In particular, wedges in the group indicated by arrow 106 contact the surface 104, while wedges in the group indicated by arrow 107 contact the surface 105. The surfaces 104,105 are inclined for example at an angle of approximately 15° with respect to a plane extending between the wedges and including the longitudinal operational axis 15 of the load frame 10. When fluid is provided in the chamber on a lower side of each piston 51-54, cylinder body 56 moves relative to the pistons 51-54 so as to move the wedges of each pair towards each other. Likewise, when fluid is provided in the chamber on an upper side of the pistons 51-54, the cylinder body 56 moves upwardly, thereby allowing the wedges to move away from each other, for example, under the spring force provided by the springs 96. FIG. 5 illustrates this operation; however, it should be noted that sides of cylinder body 56 illustrated show two positions. The side having the ports 81 and 82 illustrates the position of the cylinder body 56 with the wedge in its most open position, while the other side of the cylinder body 56 illustrates the position of the wedge in a position so as to engage the test specimen.

By way of example, test specimen holder 17 can be configured with multiple grip assemblies (e.g. 41-44) so as to be able to grip a test specimen approximately one meter wide. Although test specimen holders having multiple grip assemblies with a length capable of gripping test specimens greater or less than one meter can also be made.

Advantageously, each of the pistons 51-54 are secured together in the exemplary embodiment so that they act in unison, thus the full load capability of the test specimen holder 17 can be applied to the test specimen irregardless of the number of pairs of wedges 91-94 actually gripping the test specimen.

In the embodiment illustrated, it can be advantageous that an even number of gripping assemblies 41-44 be used in the test specimen holder 17 so that an equal number of gripping assemblies are provided on each side of the longitudinal operational axis 15 of the load frame 10 so as, for example, to efficiently apply torsion loads.

It should also be noted that the wedge pairs 91-94 can be supported directly on the corresponding pistons if desired as illustrated in FIG. 5.

Figure 6:
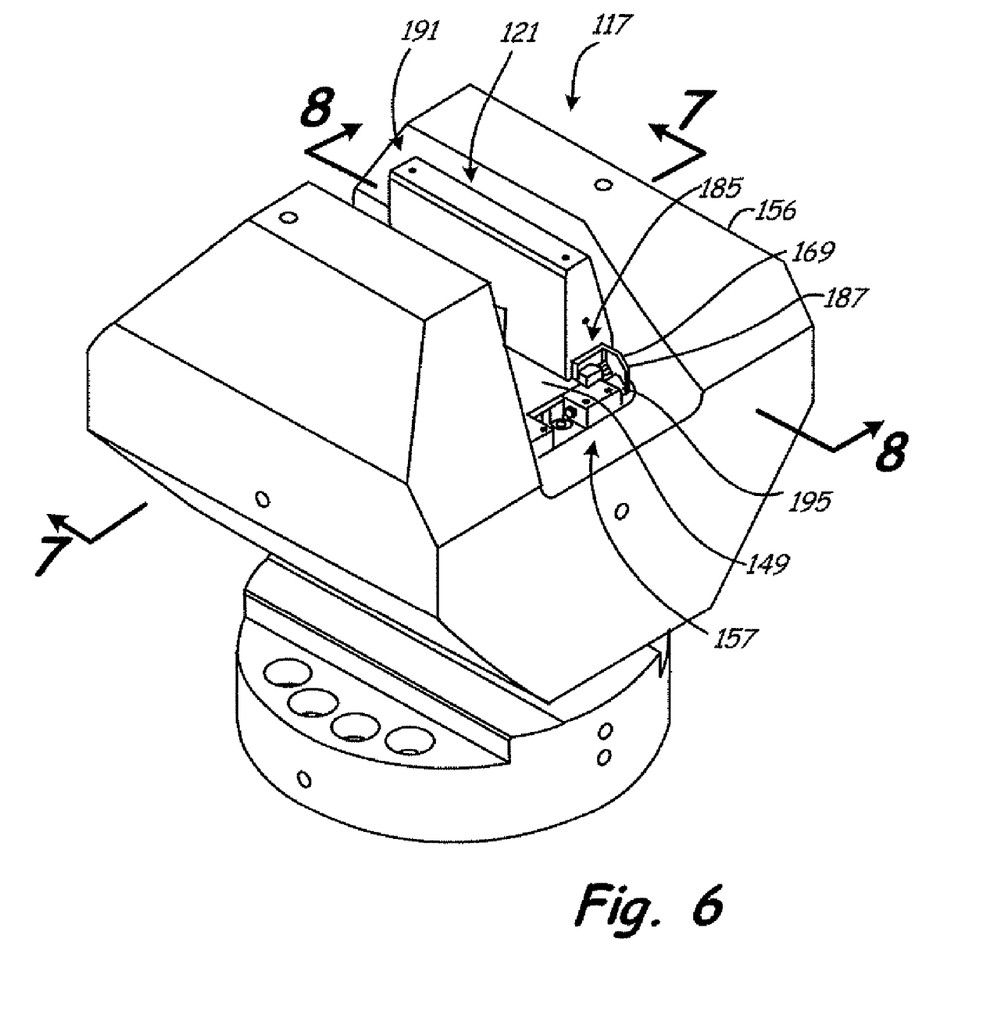
FIG. 6 is a perspective view of a second embodiment of a test specimen holder.
Figure 7:
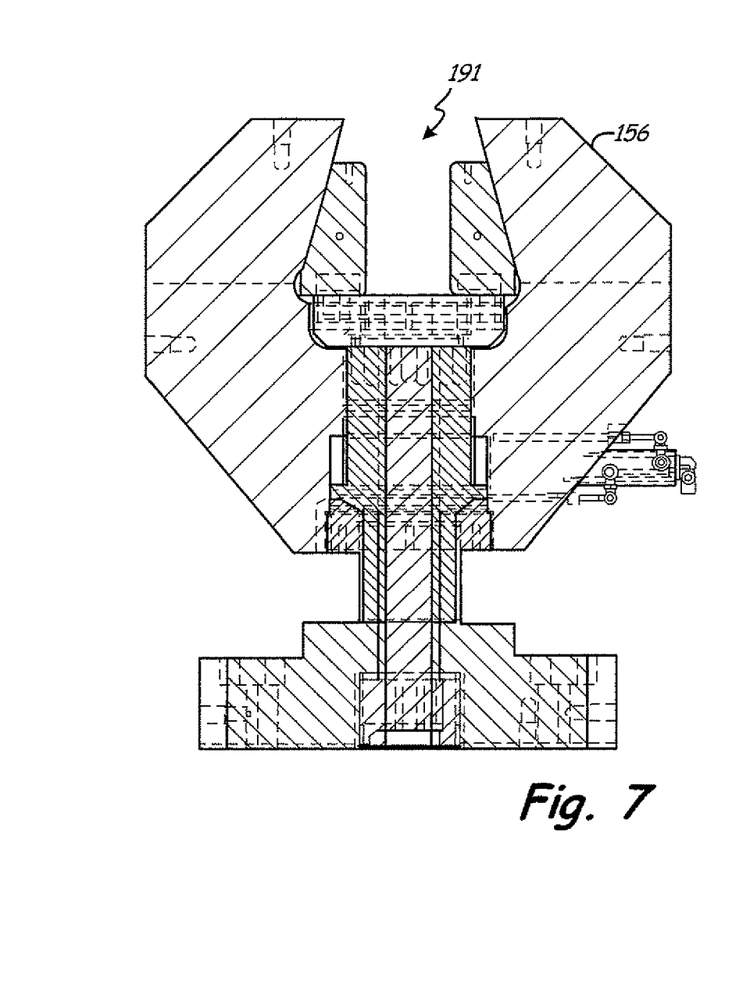
FIG. 7 is a sectional view of the test specimen holder of FIG. 6 taken along lines 7-7 of FIG. 6.
Figure 8:
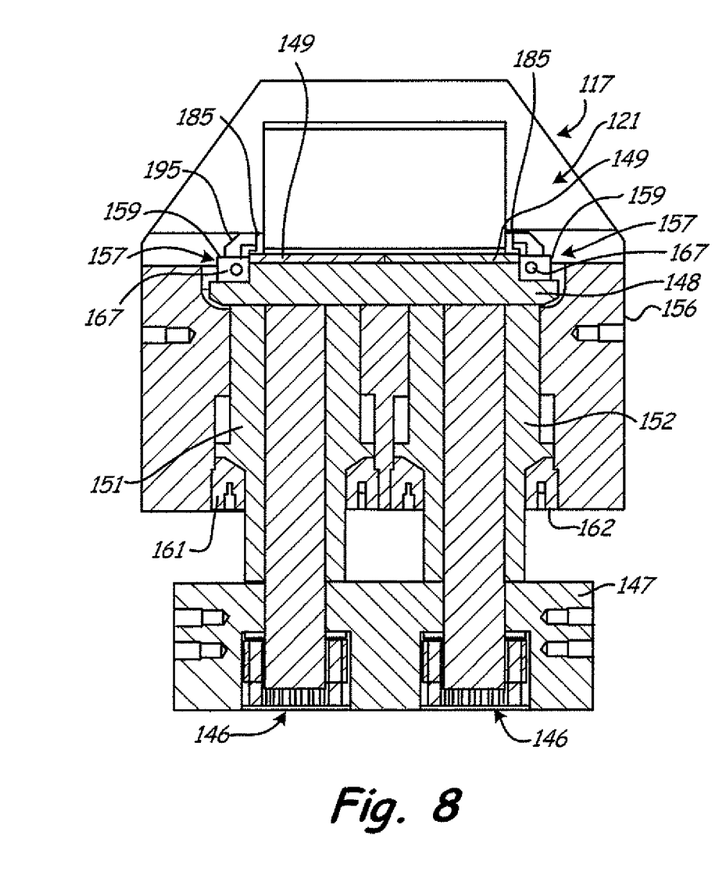
FIG. 8 is a sectional view of the test specimen holder of FIG. 6 taken along lines 8-8 of FIG. 6.

It should also be noted that any combination of multiple pairs 91-94 of opposed wedges and multiple pistons 51-54 can be used, particularly if a wedge plate 48 joins each of the pistons together and serves as a support surface for the wedges. This is illustrated in FIGS. 6-8. Furthermore, if a wedge plate 48 is used, the opposed wedge pairs need not be aligned with an axis of the pistons 51-54 such as illustrated. However, in order to provide possible desired loading on the test specimen, the opposed wedge pairs 91-94 are arranged on the wedge plate 48 with minimal gaps formed between each adjacent pair of opposed wedges.

FIGS. 6-8 illustrate a second embodiment of a test specimen holder 117. In FIGS. 6-8 and in the description below similar components to those described above are identified with reference numbers increased by one hundred. For example, cylinder body 156 is similar in function to cylinder body 56 described above.

In the embodiment illustrated, test specimen holder 117 includes a gripping assembly 121 having pistons 151 and 152 secured to a tie bar (herein wedge plate 148 and mounting plate 147) with fasteners 146 and disposed in sealed chambers having end caps 161 and 162. However, in this embodiment, one pair of wedges 191 is provided to engage and grip the test specimen when actuated by relative movement of the cylinder body 156 to the pistons 151 and 152. The wedges 191 can be quite long, for example, one foot in length although lengths shorter and longer can also be made.

In this exemplary embodiment, the wedges 191 slide upon one or more wear plates 149 (herein two are illustrated), although the wedges 191 are supported by the wedge plate 148. The wear plates 149 are secured to the wedge plate 148 with suitable fasteners disposed below the wedges 191. The wear plates 149 are removable in order that they can be easily replaced in the event of damage or excess wear. The use of a plurality of wear plates 149 such as two herein illustrated can be advantageous in that the gaps between the wear plates 149 allow slight relative movement between the plates. For example, the plates 149 may be made of a hard but somewhat brittle material. With two pistons 151 and 152 secured to the wedge plate 148 there may be slight bending of the wedge plate 148, which in turn may cause undesirable stress or cracking of a single wear plate 149. Nevertheless, a single wear plate can be used in some applications, if desired. It should also be noted wear plates can be removably to the pistons, where the wedges can slide on the wear plates.

Actuator assemblies 157 move each of the wedges 191 to an open position away from each other.

The actuator assemblies can operate using hydraulic, pneumatic, electric and/or via a spring. In the embodiment illustrated, a compression spring is used and is supported in a housing 159 and urges each respective wedge 191 away from the other wedge by urging a push rod 167 against a flange 169 secured to the wedge 191. In view of the length and/or mass of each wedge 191, multiple actuator assemblies can be used. In one embodiment, an actuator assembly is provided on each side of each of the wedges 191 so as to cause substantially equal movements of each end. In addition, guide assemblies 185 can be provided to both retain and/or guide each of the wedges 191. The guide assemblies 185 include a track and an element cooperative with the track. In the embodiment illustrated, a track 187 is provided on each side of each wedge 191 with an element 195 secured in a fixed position relative to the track 187. If desired, the track 187 can be disposed in a fixed position and element 195 can be attached to the wedge 191. In one embodiment, the engaging elements (e.g. engaging flanges) of the track and element are arranged so as to retain the wedges on the surface they slide on (e.g. wear plate 149, wedge plate 148, piston surface) and inhibit separation therefrom even if the holder 117 is held upside down. A similar concept can be used in the guide assemblies described above in the previous embodiment such that engaging flanges inhibit separation of the wedges from the surface they slide upon even if held upside down.

Figure 9:
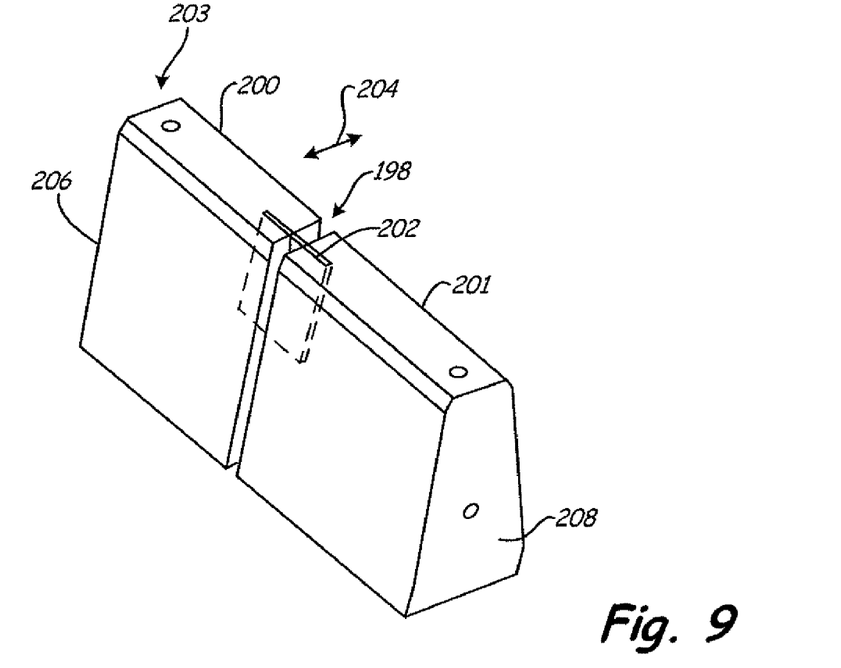
FIG. 9 is a pair of wedges joined with a first coupler.
Figure 10:
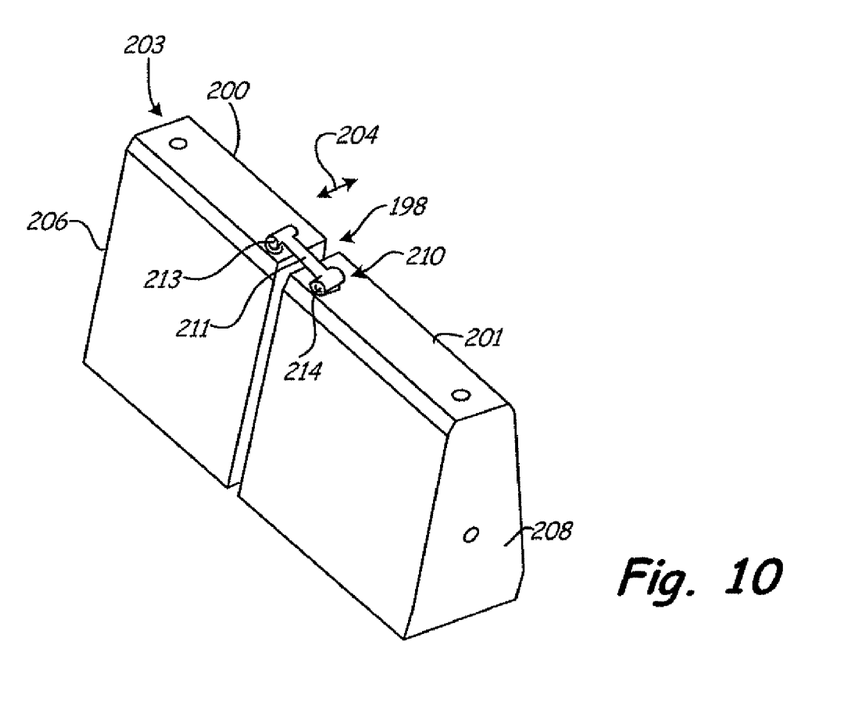
FIG. 10 is a pair of wedges joined with a second coupler.

FIGS. 9 and 10 illustrate a coupler 198 that can be used if desired to link two wedges 200 and 201 together to form a wedge assembly 203, the wedges 200 and 201 being used on the same side of the test specimen such as in group 106 or group 107. In FIG. 9, the coupler comprises a flexible plate 202 joined at each end to wedges 200 and 201 and spanning the gap therebetween. The plate 202 allows a small amount relative movement in the direction indicated by double arrow 204, but otherwise keeps the ends of the wedges 200 and 201 joined together so that the actuator assemblies 157 or springs 96 described above can be used on the remote ends 206 and 208 of wedges 200 and 201, respectively, in order to urge the wedge assembly 203 to move.

FIG. 10 illustrates the coupler 198 comprising a link assembly 210 having a link element 211 secured to each of the wedges 200 and 201 on pins 213 and 214, respectively. Like the flexible plate 202, the link assembly 210 allows a small amount relative movement in the direction indicated by double arrow 204, but otherwise keeps the ends of the wedges 200 and 201 joined together so that the actuator assemblies or springs 96 described above can be used on the remote ends 206 and 208 of wedges 200 and 201, respectively, in order to urge the wedge assembly 203 to move. As appreciated by those skilled in the art, other forms of couplers can also be used. In addition, more than two wedges can be coupled together to form a wedge assembly 203 and more than one wedge assembly 203 can be used in each group 106 or 107.

Although the subject matter has been described in language specific to structural features and/or methodological acts, it is to be understood that the subject matter defined in the appended claims is not limited to the specific features or acts described above as has been held by the courts. Rather, the specific features and acts described above are disclosed as example forms of implementing the claims.

What is claimed is:

1. A test specimen holder, comprising:
a cylinder body having a chamber, the cylinder body having first and second inclined surfaces facing each other;
a first group of wedges and a second group of wedges, each group of wedges having a pair of wedges wherein each wedge has an inclined surface, wherein the inclined surfaces of the first group of wedges engages the first inclined surface of the cylinder body, and wherein the inclined surfaces of the second group of wedges engages the second inclined surface of the cylinder body; and
a piston supporting the groups of wedges, the piston being disposed in the chamber, the cylinder body being operable with the piston and the wedges to urge the groups of wedges together with relative movement of the cylinder body with respect to the piston when the chamber is pressurized, wherein each of the wedges moves with respect to the piston and the cylinder body so as to engage a test specimen during relative movement of the cylinder body with respect to the piston when the chamber is pressurized, and wherein the first group of wedges move together and the second group of wedges move together.

2. The test specimen holder of claim 1, further comprising at least two springs, wherein a first spring is configured for urging a wedge of the first group of wedges against the first inclined surface of the cylinder body, and a second spring is configured for urging a wedge of the second group of wedges against the second inclined surface of the cylinder body.

3. The test specimen holder of claim 1, further comprising a plurality of springs, wherein a spring is provided on each side of each wedge and configured to urge the wedge against the corresponding inclined surface of the cylinder body.

4. The test specimen holder of claim 1, further comprising a plurality of guide assemblies, wherein a guide assembly is provided on a side of at least some of the wedges, the guide assemblies configured to allow guided movement of the opposed wedges toward and away from each other and limit movement of the wedges transverse to the guided movement.

5. The test specimen holder of claim 1, wherein each guide assembly comprises a guide element on a side of the wedge and a guide element fixed relative to a surface the wedge slides on.

6. The test specimen holder of claim 1, further comprising a coupler joining together adjacent wedges from each pair of wedges.

7. The test specimen holder of claim 1, wherein movement of the first and second groups of wedges towards each other is in a first direction, the test specimen holder further comprising means for limiting lateral movement of the wedges transverse to the first direction.

\* \* \* \* \*